United States Patent
Xu et al.

(10) Patent No.: US 7,074,774 B2
(45) Date of Patent: Jul. 11, 2006

(54) USE OF N-ACETYL-D-GLUCOSAMINE IN THE MANUFACTURE OF PHARMACEUTICAL USEFUL FOR TREATING CARDIO-CEREBROVASCULAR ANOXEMIA

(75) Inventors: Qiwang Xu, Chongqing (CN); Junkang Liu, Chongqing (CN); Zetao Yuan, Chongqing (CN)

(73) Assignees: Third Military Medical University Chinese People's Liberation Army, Chongquing (CN); Bio-Wave Institute of Suzhou Hi-Teach New District Corporation Ltd., Suzhou Jiangsu (CN)

(*) Notice: Subject to any disclaimer, the term of this patent is extended or adjusted under 35 U.S.C. 154(b) by 0 days.

(21) Appl. No.: 10/469,213

(22) PCT Filed: Feb. 28, 2002

(86) PCT No.: PCT/CN02/00123

§ 371 (c)(1),
(2), (4) Date: Jan. 12, 2004

(87) PCT Pub. No.: WO02/067949

PCT Pub. Date: Sep. 6, 2002

(65) Prior Publication Data

US 2004/0106577 A1   Jun. 3, 2004

(30) Foreign Application Priority Data

Feb. 28, 2001   (CN) .................................. 01104893

(51) Int. Cl.
*A01N 43/04*   (2006.01)
*A61K 31/70*   (2006.01)

(52) U.S. Cl. ........................................................ 514/62

(58) Field of Classification Search .................. 514/62
See application file for complete search history.

(56) References Cited

U.S. PATENT DOCUMENTS 4,696,919 A * 9/1987 Hinohara et al. ............. 514/62

FOREIGN PATENT DOCUMENTS

| CN | 1156026 | 8/1997 |
| CN | 1156027 | 8/1997 |
| CN | 1156028 | 8/1997 |
| WO | 93/14765 | 8/1993 |
| WO | 93/18775 | 9/1993 |

OTHER PUBLICATIONS

Collard, C.D, et al. "Complement Activation after Oxidative Stress Role of the Lectin Comlement Pathway" American Journal of Pathology, vol. 156 No. 5 (2000) pp. 1549-1556.

* cited by examiner

*Primary Examiner*—Shaojia Anna Jiang
*Assistant Examiner*—Traviss C. McIntosh, III
(74) *Attorney, Agent, or Firm*—Ladas and Parry LLP

(57) ABSTRACT

The present invention has disclosed a use of N-acetyl-D-glucosamine in the manufacture of a medicament for resisting cardiac and cerebral ischemia and oxygen-deficiency. N-acetyl-D-glucosamine can obviously prolong the survival time of the experimental animal under the condition of cerebral ischemia and oxygen-deficiency at normal pressure, can decrease cerebral edema degree and other symptoms of the nerve behavior caused by cerebral ischemia and re-infusion.

2 Claims, No Drawings

USE OF N-ACETYL-D-GLUCOSAMINE IN THE MANUFACTURE OF PHARMACEUTICAL USEFUL FOR TREATING CARDIO-CEREBROVASCULAR ANOXEMIA

TECHNICAL FIELD

The present invention relates to the use of N-acetyl-D-glucosamine and pharmaceutical acceptable salts thereof in the manufacture of a medicament for resisting cardiac and cerebral ischemia as well as oxygen-deficiency.

BACKGROUND ART

The cardiac and cerebral ischemia as well as oxygen-deficiency is clinically a common phenomenon, for instance, the heart disease caused by ischemia and oxygen-deficiency of the cardiac muscle due to heart coronary artery constriction or occlusion, and the cerebral disease caused by constriction or occlusion of the cerebral vessels, which is characterized by ischemia and oxygen-deficiency. Over a long period of time, people have worked all along for finding various medicaments which are able to effectively cure the diseases related to ischemia and oxygen-deficiency.

In the research of "bio-waves" theory, the present inventor has set up a bacterial wave growth model. Through researching, it is known that this wave is of its intrinsic regulation mechanism: some chemical substances are able to participate the regulation in the bio-wave process, so as to transform an abnormal periodic slow wave into a normal physiological chaotic quick wave, and this kind of substances are known as promoting wave factors. Through separating, purifying and identifying, it is determined that one of the factors is N-acetyl-D-glucosamine, the promoting wave function of which is shown in lubricating and protecting the cell. Many biochemical and physiological process of human body need the participation of the promoting wave factors, and it would lead to an abnormal state, if this kind of promoting wave factors is lacked in the living body.

N-acetyl-D-glucosamine is a chemical reagent. From the 1990's, it is continually used to treat pericementitis (WO9102530A1), microbiological infection (WO9718790A3), intestinal inflammation (WO9953929A1), cornea disease (JP10287570A2), hypertrophy of the prostate (US05116615) and so on. It is also applied in cosmetology (JP59013708A2), shampoo preparation (JP2011505A2), tissue growth regulation agent (WO/A 8 702244), and etc., but it has not been used in the manufacture of a medicament for resisting cardiac and cerebral ischemia as well as oxygen-deficiency up to now.

The applicant of the present invention is surprised to find that N-acetyl-D-glucosamine and pharmaceutical acceptable salts thereof are able to obviously prolong the survival time of experimental animals under the condition of cerebral ischemia and oxygen-deficiency at normal pressure, to decrease cerebral edema degree and other symptoms of the nerve behavior caused by cerebral ischemia and re-infusion. Therefore, for human beings and animals, it can be used for resisting the condition of cardiac and cerebral ischemia as well as oxygen-deficiency, preventing and treating the diseases related to cardiac and cerebral ischemia as well as oxygen-deficiency.

CONTENTS OF THE INVENTION

Therefore, the present invention is related to the use of N-acetyl-D-glucosamine and pharmaceutical acceptable salt thereof in the manufacture of a medicament for resisting cardiac and cerebral ischemia and oxygen-deficiency In addition, the present invention is related to a method for preventing or treating the diseases related to cardiac and cerebral ischemia as well as oxygen-deficiency, including administrating to a patient who is in need thereof an effective amount of N-acetyl-D-glucosamine and pharmaceutical acceptable salts thereof to prevent and treat the diseases related with cardiac and cerebral ischemia as well as oxygen-deficiency.

The molecular formula of N-acetyl-D-glucosamine is $C_8H_{15}NO_6$, its structure is as follows:

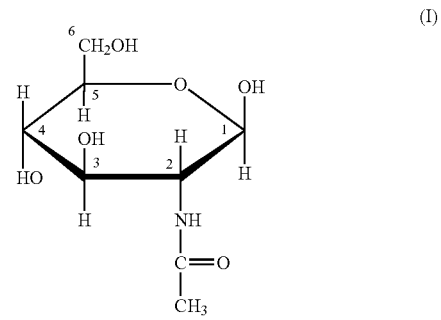

(I)

N-acetyl-D-glucosamine can be purchased in the market or prepared according to known methods. For instance, patent application WO97/31121 has disclosed a method for preparing N-acetyl-D-glucosamine from chitin by enzyme method, Japanese patent application JP63273493 has disclosed a method in which chitin is partially hydrolyzed into N-acetyl-chitose, and then it is treated with enzyme to obtain N-acetyl-D-glucosamine.

The pharmaceutical acceptable salts of N-acetyl-D-glucosamine that can be mentioned are the salts formed with pharmaceutical acceptable acids, for instance, the salts formed with inorganic acids, such as hydrochloride, hydrobromide, borate, phosphate, sulfate sulfite and hydrophosphate, and the salts formed with organic acids, such as citrate, benzoate, ascorbate, methyl sulfate, naphthalene-2-sulfonate, picrate, fumarate, maleate, malonate, oxalate, succinate, acetate, tartrate, mesylate, tosylate, isethionate, α-ketoglutarate,α-glyceryl phosphate and glucose-1-phosphate.

Generally, the compound of the present invention is administrated by oral, parenteral, sublingual or penetrating skin, preferably administrating the medicament parenterally or orally. In the course of treating diseases related with cardiac and cerebral ischemia as well as oxygen-deficiency according to the present invention, the amount of the active component to be taken is dependent upon the features and seriousness of the diseases and the weight of the patient body. For the adults, the commended dosage for injection administration is 2.5 mg/kg. The reference dosage for oral administration is 5 mg/kg.

The pharmaceutical composition of the invention for treating the indication mentioned above are suitable for administration by oral, sublingual, subcutaneous, intra-muscle, intravein, penetrating skin, or rectum, the active component is able to be applied to animals and human beings in the form of dosage unit, such as in the form of freeze drying product or mixed with conventional pharmaceutical carrier. A suitable unit form of administration includes oral form, such as orally dispersible tablet, capsule, powder, granule and solution or suspension; the form for administrating via sublingle or buccal; the form for administrating via subcutaneous, intramuscle or intravein; the form for local or rectum administration. The preparations for oral and parenteral administrations are preferred, particularly aqueous solution, alcoholic solution and capsule.

Solid composition in the form of tablet are made by mixing the main active component with pharmaceutial excipient, such as gelatin, starch, lactose, magnesium stearate, talc powder, Arabic gum and etc., The tablet is able to be coated with sugar or other suitable substances, or making them possess a persistent and delayed function and continually release pre-determined amount of active component.

The preparation in from of capsule can be obtained by mixing active component with diluent, and filling the obtained mixture into soft or hard capsule.

The preparation in the form of syrup or elixer may comprise active component and sweetener that would better have no caloric, methyl p-hydroxybenzoate and propyl p-hydroxybenzoate as antiseptic agent, fragrancing agent and suitable coloring material.

The water-dispersible powder and granular preparation may comprise active component, mixed with dispersing agent or wetting agent, or suspending agent, such as polyvinylpyrrolidone, and sweetener or taste regulating agent.

The suppository for rectum administration is prepared with an adhesive which is melted at the same temperature of rectum, such as cocoa oil or polyethylene glycol.

The injectable aseptic aqueous solution, salt solution, alcoholic solution or homogenous suspension of the compound of the present invention can be administrated parenterally.

OPTIMAL MODE FOR CARRYING OUT THE INVENTION

The following experimental example is used to illustrate the effect of resisting cardiac and cerebral ischemia as well as oxygen-deficiency, and the low toxicity of the compound of the present invention (the compound of formula (I)).

I. The protecting effect of N-acetyl-D-glucosamine in rat with cerebral ischemia and Re-Infusion
  1. Animal: Wistar rat provided by the $3^{rd}$ Military Medical University P.R. China. Half of them are male, the other are female.
  2. Method for making model: the model is made by four arteries ligation method to cause the rat to be cerebral ischemia, in which for each rat, the vertebra artery in the vertebra foramen of the second cervical vertebra is blocked by hot coagulation with electric coagulator, then separate the two common carotid artery in the front of it, after that, remain the surgical thread jacket, sewing up. Next day, after the animal is recovered from anesthesia, open the sewing thread in the front of the animal, clamp the two common carotid artery with artery clip, it needs 20 min. in total. The animals, which in the process of clamping have convulsion, incontinence of urine and stool and etc. as remarkable characteristics, are taken as model animals to be continually observed; but the animals, which do not appear these symptoms, are fallen into disuse.
  3. Grouping: the animals are divided into four groups (eight animals in each group)

N-acetyl-D-glucosanime Group: that is, 30 min before the carotid artery of rat is clamped, administrating N-acetyl-D-glucosanime with a dosage of 0.25 g/kg.

Astragalus Group: that is, before the animal is treated, administrating Astragalus injection solution by abdominal injection.

Astragalus+N-acetyl-D-glucosanime Group: that is, 30 min before clamping, administrating a mixture injection solution of 0.25 g/kg of N-acetyl-D-glucosanime and 2 g/kg of Astragalus by abdominal injection.

The control Group: not administrating any medicament, but injecting physiological salt solution with the same volume.

The animals in each group are all fed in standard. In the process of operation, please pay attention to asepsis.

4. Observation Indexes.

Survival:
    Abnormal ratio of the water content in the brain (by dry-wet weight method):
      Scoring the symptoms of nerve behavior
      0 score: no symptom of nerve defect, moving normally
      1 score: cannot extend the front claw at the opposite side
      2 score: when walking, the body rotates toward the hemiplegia side
      3 score: the body collapse down toward the hemiplegia side
      4 score: not capable of walking spontaneously, losing consciousness 5. Results:
    5.1 Survival:
      Control group: 62.5%; N-acetyl-D-glucosanime group: 87.5%; Astragalus group: 75%; mixture group: 75%.
    5.2 Water Content of Brain:
      Control group: 70.84%; N-acetyl-D-glucosanime group: 66.2%; Astragalus group: 69.53%; Astragalus+AWA group: 65.8%.
    5.3 Abnormal Ratio:
      Control group: 75%; N-acetyl-D-glucosanime group: 50%; Astragalus group: 50%; mixture group: 62.5%.

6. Conclusion:
    With the model made by four arteries ligation method to cause the rat to be cerebral ischemia, administrating N-acetyl-D-glucosanime with a dosage of 0.025 g/kg, after that the cerebral edema degree of rat is decreased obviously caused by cerebral ischemia and re-infusion, corresponding nerve symptoms are also released, at the same time, the survival rate is raised obviously.

II. Experimental research of the resistance to oxygen-deficiency of N-acetyl-Dglucosanime 1. Model of Oxygen Deficiency at Normal Pressure:
    The mice were put into a sealed glass desiccator with a volumn of 200 ml and charged with 20 g of sodium lime to observe the survival time.

2. Animal:
    The mice of Kunming species, provided by the $3^{rd}$ Military Medical University of P. R. China 3. Grouping:
    Two groups had 24 mice in total, in the experimental group, two weeks before experiment, administrating N-acetyl-D-glucosanime by stomach infusion with a dosage of 0.05 g/kg, in the control group, they were normally fed.

4. Result:

Average survival period of the experimental group was much longer than that of the control group.

5. Conclusion:

N-acetyl-D-glucosanime can raise the resistance to oxygen deficiency of the small mice.

III. Toxicological test of the compound of formula (I), including:
1. acute toxicity test: including tests of administrating medicine by oral, intravenous injection and maximum limit amount for administration;
2. Ames test;
3. micronucleus test of bone marrow cell of mouse;
4. abnormal sexual test for the sperm of mouse;
5. abnormal aberrance test for the chromosin of mouse's testis;
6. chronic lethal test;
7. subchronic toxicity (feed for 90 days) test;
8. traditional aberrance-inducing test;

The results from these tests show that in the acute toxicity test of the compound of formula (I), the dosage more than 2 g/kg is taken, which is 300 times than the injection dosage for human being, but the acute toxicosis reaction had not appeared yet; in the long-period toxicity test, the maximum dosage has reached up to 1 g/kg, and after the treatment and observation for four weeks, there is no toxicosis reaction yet; and in the reproduction test, the mouse was fed with routine dosages from 7 mg/kg for 3 generations, it has been proved that the compound of formula (I) has no influence on the pregnancy, birth, nurse and the growth of baby mice, so it is proved that the compound of formula (I) is a substance without toxicity.

The invention claimed is:

1. A method of treating a subject having a cardiac or cerebral ischemia or oxygen deficiency comprising administering to the subject an effective amount of a medicament comprising N-acetyl-D-glucosamine and/or a pharmaceutically acceptable salt thereof.

2. The method according to claim 1, wherein said medicament is in the form of an injection solution, tablet or capsule.

* * * * *